United States Patent [19]

Sheridan et al.

[11] Patent Number: 4,838,095
[45] Date of Patent: Jun. 13, 1989

[54] SIGHT GLASS CONSTRUCTION

[75] Inventors: Michael Sheridan, Old Bridge, N.J.; Kenneth Jaffe, Boulder, Colo.

[73] Assignee: Ethylene Corp., Murray Hill, N.J.

[21] Appl. No.: 151,169

[22] Filed: Feb. 1, 1988

[51] Int. Cl.⁴ .............................................. G01N 1/10
[52] U.S. Cl. ................................ 73/864.63; 137/551; 73/863.86
[58] Field of Search ........... 73/864.91, 864.51, 864.63, 73/863.86, 323, 325; 422/58, 68, 102; 137/551

[56] References Cited

U.S. PATENT DOCUMENTS

| | | | |
|---|---|---|---|
| 2,704,127 | 3/1955 | Haessler | 137/551 X |
| 3,531,264 | 9/1970 | Greipel | 137/551 X |
| 3,586,045 | 6/1971 | Zimmer | 137/551 |
| 3,659,629 | 5/1972 | Deaton | 137/551 |
| 4,294,800 | 10/1981 | Tavlarides et al. | 422/81 X |
| 4,671,110 | 6/1987 | de Kock | 73/323 |
| 4,762,798 | 8/1988 | Deutsch | 422/102 X |

FOREIGN PATENT DOCUMENTS

| | | | |
|---|---|---|---|
| 551849 | 1/1958 | Canada | 137/551 |
| 1942330 | 3/1971 | Fed. Rep. of Germany | 137/551 |
| 2139699 | 2/1973 | Fed. Rep. of Germany | 137/551 |

*Primary Examiner*—Tom Noland
*Attorney, Agent, or Firm*—Charles E. Temko

[57] ABSTRACT

An improved sight glass for use with sampling systems employed for testing the content of chemical reaction vessels. In addition to incorporating a check valve for preventing contamination of a vacuum source, the device incorporates provision for entrapping and draining sampled fluids in the event of leakage or fracture of the glass components thereof. This is accomplished by providing an inner transparent glass tube, the inner surface of which is chemically inert, and an outer concentric tube of synthetic resinous material which surrounds the inner tube and is less subject to breakage. The cylindrical interstice between the inner and outer tubes forms a drain for retaining leakage caused by fracture of the inner tube. A floating valve cooperates with a valve seat positioned longitudinally medially of the inner and outer tubes.

4 Claims, 2 Drawing Sheets

SIGHT GLASS CONSTRUCTION

BACKGROUND OF THE INVENTION

This invention relates generally to the field of chemical processing of corrosive fluids, and more particularly to an improved sight glass construction forming part of a vacuum-powered sampling means used to check the progress and condition of a reacting mass of material within a reaction vessel. Reference is made to U.S. Pat. No. 4,594,903 dated June 17, 1986 which discloses a system for accomplishing periodic sampling which includes a transparent sight glass through which a portion of a sample drawn from a reaction vessel may be viewed.

The typical sight glass, while adequately resistant to the effects of corrosive fluids is also quite fragile, and should breakage occur, the resultant leakage can result in serious damage. Further leakage can often occur as a result of failure of a check valve which normally prevents the flow of corrosive fluid therepast to result in contamination of the vacuum system used to withdraw fluid from the vessel.

SUMMARY OF THE INVENTION

Briefly stated, the invention contemplates the provision of an improved sight glass construction of the type described in which provision has been incorporated for preventing the escape of corrosive reacting fluids in the event of fracture or other breakage of the glass components thereof. As contrasted with prior art constructions, the sight glass includes a first inner tubular element, the inner surfaces of which are normally chemically resistant, and an outer tubular element which surrounds the inner element and forms an interstice therebetween. Drain means communicates with the interstice and collects fluids which enter the same thereby preventing spreading of the fluid outwardly of the device. As further contrasted with prior art constructions, the check valve is positioned medially of the inner tubular element rather than at an upper end thereof to visually indicate if the valve becomes inoperative.

BRIEF DESCRIPTION OF THE DRAWING

In the drawing, to which reference will be made in the specification.

DETAILED DESCRIPTION OF THE DISCLOSED EMBODIMENT

Figure 1:
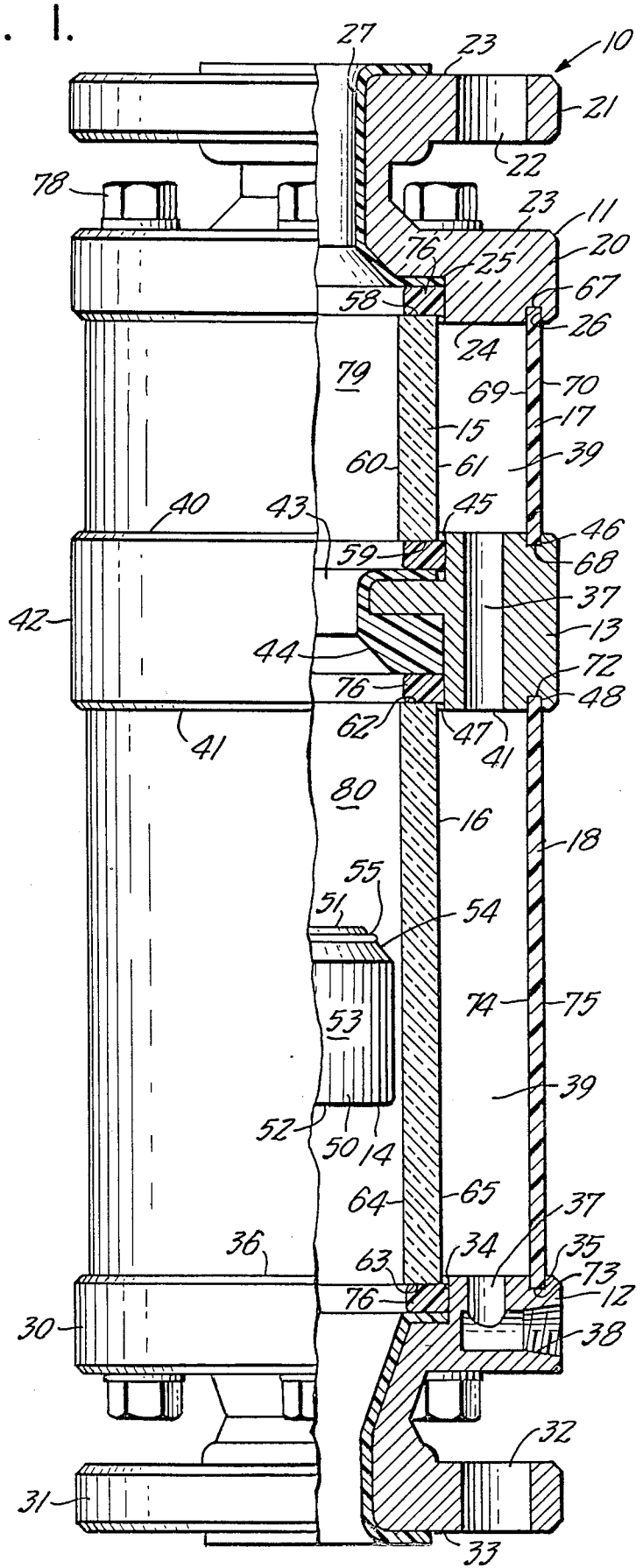
FIG. 1 is a composite elevational and longitudinal sectional view of an embodiment of the invention.

In accordance with the invention, the device, generally indicated by reference character 10 comprises: a first or upper end element 11, a second or lower end element 12, a medially positioned valve seat element 13, a check valve element 14, first and second inner tubular elements 15 and 16; and first and second outer tubular elements 17 and 18.

The upper end element 11 is preferably formed as a metallic casting, the opposed surfaces of which have been covered with teflon (polytetrafluoroethylene). It includes a main body member 20 and an integral flange member 21 having means 22 for interconnecting with a communicating fitting (not shown).

The main body member 20 is bounded by an upper surface 23 and a lower surface 24 which forms first and second curvilinear channels 25 and 26. The flange member 27 and main body member 20 form a through bore 27 which normally will be in communication with a vacuum source.

The lower end element 12 is generally similar, and includes a main body member 30, a peripheral flange member 31, interconnecting means 32 on a lower surface 33 thereof, as well as first and second circular channels 34 and 35 on an upper surface 36 thereof. Additionally, the main body 30 includes a drain conduit 37 which may include threaded means 38, the purpose of which will become more fully apparent at a point later in the disclosure. The conduit 37 communicates with an interstice 39.

The valve seat element 13 is also formed as a metallic casting, suitable teflon coated. It includes an upper surface 40, a lower surface 41 as well as a peripheral surface 42. A centrally positioned opening 43 communicates with a conical valve seat 44. The upper surface 40 forms first and second circular recesses 45 and 46. The lower surface 41 forms third and fourth recesses 47 and 48 aligned therewith.

The check valve element 14 is preferably of molded, synthetic resinous material also suitably teflon coated. It is bounded by an upper surface 51, a lower surface 52, a cylindrical side surface 53 and a conical surface 54 which corresponds to the valve seat 44. An O-ring is seated in a groove in the surface 54, and is preferably formed of fluorinated rubber so as to be substantially chemically inert.

The first inner tubular element 15 is of hollow cylindrical configuration and is formed of chemically resistant glass. It is bounded by first and second end surfaces 58 and 59, an inner surface 60 and an outer surface 61. The second inner tubular element 16 is generally similar, although substantially axially longer and is bounded by first and second end surfaces 62 and 63, as well as an inner surface 64 and an outer surface 65.

The first outer tubular element 17 is positioned concentrically with the corresponding inner element 15. As contrasted with that element, it is preferably formed from transparent synthetic resinous materials, and is bounded by first and second end surfaces 67 and 68, as well as an inner surface 69 and an outer surface 70. Likewise, the second outer tubular element 18 is bounded by first and second end surfaces 72 and 73, an inner surface 74 and an outer surface 75. During assembly, a liquid tight fit relative to the elements 15 and 16 is accomplished by the use of fluorinated rubber or teflon gaskets 76, which will normally not be required in the case of the elements 17 and 18. The entire device 10 is maintained in assembled condition by conventional bolt means 78.

It will be noted that in order to determine that the device is functioning properly, the valve seat element 13 is positioned intermediate the upper and lower end elements 11 and 12, thus forming an upper chamber 79 and a lower chamber 80. With the application of vacuum, sampled fluid (not shown) will enter the lower chamber 80 and as the level of the same rises, the check valve element 14 will float up to engagement with the valve seat element 13. Should any fluid flow into the upper chamber 79, it will be apparent that the valve element 14 is not functioning properly and the application of vacuum can be immediately discontinued. Should a rupture occur in either the first or second inner tubular elements 15 and 16, fluid will flow into the interstice 39, the upper and lower portions of which communicate through a channel 81, to be collected through the drain conduit 37 for suitable disposal. On the occurrence of such an event, since the outer tubular elements 17 and 18 are possessed of greater resiliency, the fracture of the inner tubular elements will not result in a similar fracture in the outer elements.

Thus, the device provides for accommodation for any type of malfunction likely to occur during use. Normally, a sample will not be drawn without the manual initiation of a worker, who is in a position to observe the sample, and simultaneously to observe whether or not the check valve is operative. Should a fracture occur in the inner tubular elements, for whatever reason, sampled fluids are not allowed to spread outside the device, but are immediately drained for safe disposal.

Figure 2:
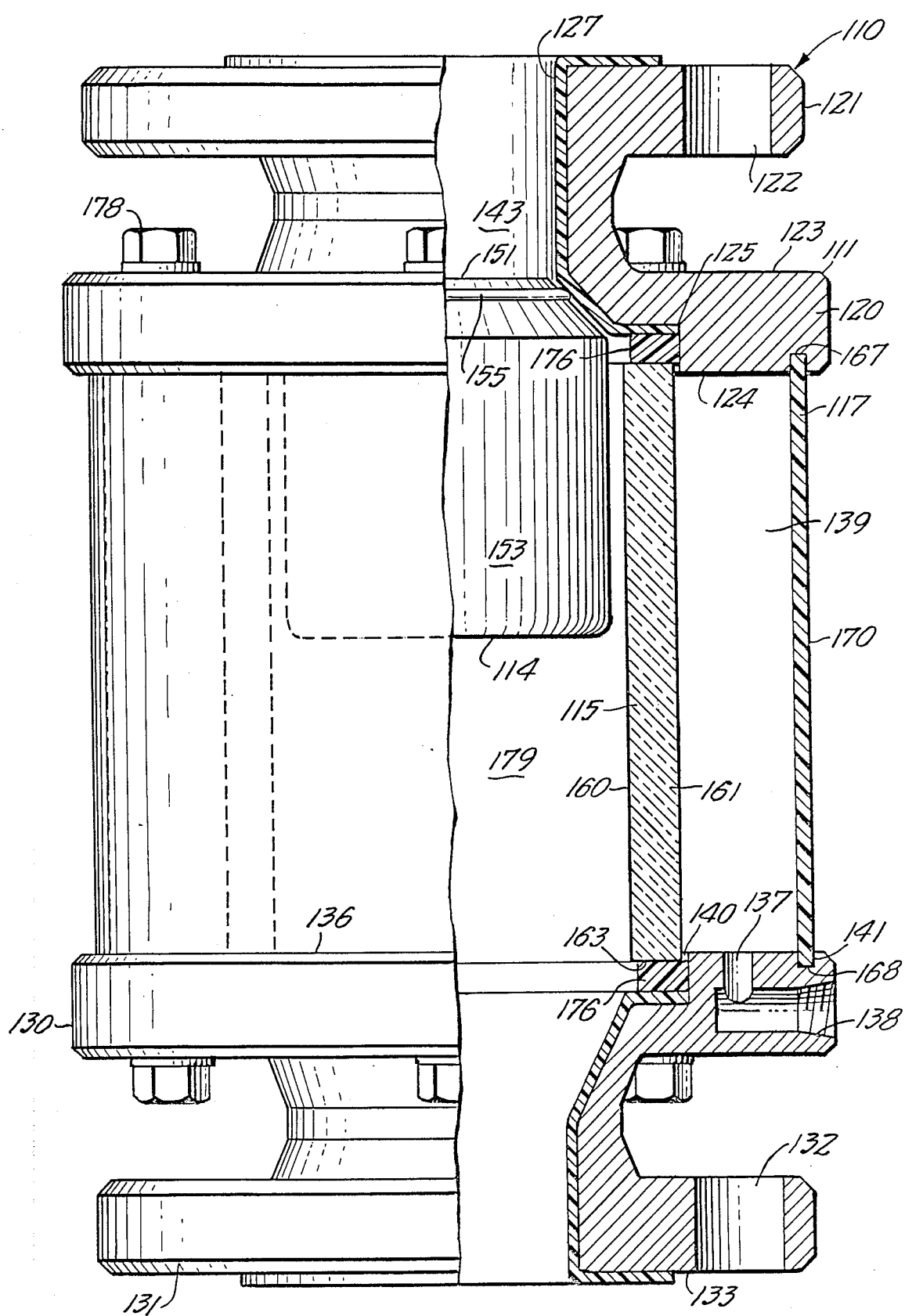
FIG. 2 is a similar composite view showing an alternate form of the embodiment.

Turning now to the alternate form of the embodiment illustrated in FIG. 2, parts corresponding to those of the form in FIG. 1 have been designated by similar reference characters with the additional prefix "1".

The alternate form differs from the principal form solely in the elimination of a separate medially positioned valve seat element 13, and the incorporation of the function of that element into the upper end element 111, thus making possible a device of somewhat reduced length. In the case of the alternate form, the operation of the check valve element 114 may be observed by noting the location of the same relative to the upper end element 11, although it will not be possible to determine whether a degree of seepage past the check valve element 114 occurs.

We wish it to be understood that we do not consider the invention limited to the precise details of structure shown and set forth in this specification, for obvious modifications will occur to those skilled in the art to which the invention pertains.

We claim:

1. An improved sight glass for sampling fluids, comprising: first and second end elements, a first inner transparent tubular element of chemically resistant material interconnecting said end elements to form a chamber for retaining fluids for visual examination, a second outer transparent tubular element interconnecting said end elements in substantially coaxial relation relative to said first tubular element to define a cylindrical interstice therebetween in non-communicating relation relative to said chamber, one of said end elements having fluid drain means incorporated therein communicating with said interstice whereby upon the fracture of said inner tubular element during use, fluids within said chamber will flow into said interstice to be collected by said fluid drain means.

2. An improved sight glass as set forth in claim 1, further comprising floating valve means within said chamber for preventing the flow of fluid outwardly of said chamber through one of said end elements.

3. An improved sight glass as set forth in claim 2, further comprising a valve seat element positioned medially of said end elements to form first and second chambers on either side thereof, said valve seat element in cooperation with said floating valve means serving to confine the flow of fluid to one of said chambers, and permitting visual examination of the operation of said floating valve means.

4. An improved sight glass as set forth in claim 2, further characterized in said inner tubular element being formed of glass, and said outer tubular element being formed of a synthetic resinous material.

* * * * *